United States Patent [19]

Tremblay et al.

[11] Patent Number: 4,664,855

[45] Date of Patent: May 12, 1987

[54] METHOD FOR PRODUCING AMALGAMABLE ALLOY

[75] Inventors: David L. Tremblay; Kamal Asgar, both of Ann Arbor, Mich.

[73] Assignee: Special Metals Corporation, New Hartford, N.Y.

[21] Appl. No.: 796,813

[22] Filed: Nov. 12, 1985

[51] Int. Cl.$^4$ ............................................. B29B 9/00
[52] U.S. Cl. ................................. 264/11; 75/0.5 C; 264/12; 420/502
[58] Field of Search .................. 264/11, 12; 75/0.5 C, 75/0.5 B, 0.5 R; 420/502, 470, 560

[56] References Cited

U.S. PATENT DOCUMENTS

| | | | |
|---|---|---|---|
| 3,305,356 | 2/1967 | Youdelis | 75/0.5 B |
| 3,588,951 | 6/1971 | Hegmann | 425/7 |
| 3,871,876 | 3/1975 | Asgar et al. | 75/169 |
| 3,997,329 | 12/1976 | Aliotta | 420/502 |
| 4,374,085 | 2/1983 | Asgar et al. | 420/470 |
| 4,479,823 | 10/1984 | Hohmann | 264/11 |

OTHER PUBLICATIONS

"Marginal Leakage of Dental Amalgam" by F. Fanian, F. Hadavi and K. Asgar—Aug. 11, 1983, Operative Dentistry.

"Creep and Corrosion of Amalgam" by D. B. Mahler, J. E. Adey and M. Marek, Journal of Dental Research, 61:33, Jan. 1982.

"Corrosion Test for Dental Amalgam" by M. Marek, Journal of Dental Research, 59:63, Jan. 1980.

*Primary Examiner*—Jan H. Silbaugh
*Assistant Examiner*—Mary Lynn Fertig
*Attorney, Agent, or Firm*—Robert F. Dropkin

[57] ABSTRACT

A process for manufacturing an atomized amalgamable alloy having mold adaptation characteristics superior to other atomized alloys and comparable or better than those for ad-mixed type alloys (alloys which are mixtures of spherical and irregularly shaped particles), and physical properties comparable to ad-mixed alloys. The process includes the steps of: producing a melt of an amalgamable alloy; atomizing the alloy so as to form particles which are primarily irregular in shape; collecting the particles; drying the particles; mechanically working the particles so as to fracture and change their shape; classifying the particles to finer than 53 microns; heat treating the particles; and reducing oxides from the surface of the particles.

6 Claims, No Drawings

METHOD FOR PRODUCING AMALGAMABLE ALLOY

The present invention relates to a method for producing an amalgamable alloy and alloy produced thereby.

Two basic methods are currently employed to produce amalgamable dental alloys. One of the methods is known as lathe cutting. The other method is known as atomization.

Lathe-cut dental alloys are typically manufactured by producing a melt of an amalgamable alloy, casting the alloy into an ingot, homogenizing the ingot at an elevated temperature, cutting the ingot into particles, ball milling the particles to further reduce their size and heat treating the particles so as to obtain desired working time and physical properties. The particles are typically classified finer than 90 microns.

Atomized dental alloys are manufactured by producing a melt of an amalgamable alloy in a crucible, releasing a stream of the molten metal from the crucible, spraying the stream with a high-pressure atomizing medium thereby forming particles of the alloy, drying the particles and heat treating the particles so as to obtain desired working time and physical properties. The atomizing medium could be a gas or a liquid or combination thereof. The particles may be spherical or somewhat irregular in shape. Particle shape is dependent upon alloy chemistry, atomizing medium and the pressure of the atomizing medium. The particles are typically classified finer than 44 microns.

As one might expect, lathe-cut and atomized dental alloys each have some advantages and disadvantages over the other. A better understanding of the respective advantages and disadvantages is obvious from a description of what takes place during amalgamation.

Amalgamable dental alloys are basically alloys of silver and tin with typical additions of copper and possible additions of other elements such as indium, zinc and palladium. These alloys are supplied to dentists in particle form. Dentists add mercury to the alloy particles and triturate the mixture in an amalgamator to form an amalgamated mass which they, in turn, condense into cavities. Mercury reacts with silver and tin, forming compounds of silver-mercury and tin-mercury. The amount of mercury added by the dentist is not, however, sufficient to complete the reaction. As a result, mercury only reacts with the surface of the alloy particles. The core of the particles remains in the unreacted state. The amalgamated mass placed by a dentist in a cavity is, after hardening, therefore, a heterogeneous material of at least three distinct phases: silver-mercury; tin-mercury; and silver-tin. The phases are, respectively, for convenience purposes, called gamma one, gamma two and gamma. When properties of the three phases are compared, it is found that the strength and corrosion resistance are highest for the gamma phase and lowest for the gamma two phase. Relative ratios of these three phases, as well as the shape and size of the original alloy particles that are left in the final product, determine the physical properties of amalgamated dental alloys as well as their ease of manipulation.

The respective advantages and disadvantages of irregularly shaped particles of lathe-cut, and spherically shaped particles of atomized, dental alloys are as follows:

(1) Irregularly shaped particles can be more adaptable to filling the spaces adjacent to cavity walls than are spherical particles, and, as a result thereof, produce amalgam restorations which are less susceptible to leakage of oral fluid into the cavity. Leakage of oral fluid into the cavity contributes to post-operative sensitivity and a possible recurrence of decay. The adaptability of the irregularly shaped particles is attributable to their shape and the greater condensing force necessitated thereby.

(2) More dentists are used to working with lathe-cut irregularly shaped particles than atomized spherically shaped particles, as lathe-cut alloys have been in the market a much longer period of time which is, in fact, over one hundred years.

(3) In general, for any given chemistry, atomized spherically shaped particles produce stronger amalgam restorations than do lathe-cut irregularly shaped particles. Irregularly shaped particles have a higher surface-to-volume ratio and, as a result thereof, require more mercury during trituration. They, accordingly, form more of the weaker silver-mercury and tin-mercury phases at the expense of the stronger silver-tin phase.

(4) Amalgam restorations formed from atomized spherically shaped particles are usually smoother than those formed from lathe-cut irregularly shaped particles as the size of the spherical particles is generally less than the size of the irregular particles.

(5) Atomized particles are usually cleaner than lathe-cut particles. Lathe-cut particles often contain a higher percentage of oxides and other undesirable elements.

(6) Particles from lathe-cut alloys have minute cracks. Mercury can penetrate some of these cracks during trituration, react with the alloy and repair the crack. Dirty surfaces can, however, preclude such a reaction. As a result, mercury can be trapped in the crack, resulting in a slower rate of reaction and lower initial physical properties.

(7) Atomized spherical particles take less force to condense than do irregularly shaped particles. The reduced force is advantageous to both dentist and patient.

(8) In general, amalgams produced from lathe-cut alloys shrink to a lesser degree than do those produced from spherical alloys of the same composition.

The present invention provides a process for manufacturing an atomized amalgamable alloy having mold adaptation characteristics superior to other atomized alloys and comparable or better than those for ad-mixed alloys (alloys which are mixtures of spherical and irregularly shaped particles), and physical properties comparable to ad-mixed alloys. The better the mold adaptation characteristics, the less susceptible are amalgam restorations to leakage of oral fluid into a cavity. Leakage of oral fluid contributes to post-operative sensitivity and possible reoccurrence of decay.

It is accordingly an object of the present invention to provide a method for producing an amalgamable alloy.

The process of the present invention comprises the steps of: producing a melt of an amalgamable alloy; atomizing the alloy so as to form particles which are primarily irregular in shape; collecting the particles; drying the particles; mechanically working the particles so as to fracture and change their shape; classifying the particles to finer than 53 microns; heat treating the particles; and reducing oxides from the surface of the particles.

Those skilled in the art know how to produce irregularly shaped atomized particles. Particle shape is dependent upon such factors as the difference in surface energy between molten metal and the atomizing medium as well as the pressure of the atomizing medium. The presently preferred means for producing irregularly shaped particles, in accordance with the present invention, is water atomization at a pressure of from 700 to 2,300 pounds per square inch (usually 1,000 to 2,000 pounds per square inch). Particle sizes are greater at the lower pressures. Atomized particles, in accordance with the present invention, are generally larger than 150 microns in their longest dimension.

The irregularly shaped atomized particles are mechanically worked so as to fracture and change their shape. Substantially all of the particles are reduced to a size of less than 53 microns in their longest dimension after working. Various means for working the particles will be evident to those skilled in the art. One means utilizes a high-speed multiple hammer mill which is generally used to reduce the size of ores and/or minerals. A protective atmosphere may be used during working.

The mechanically worked particles are heat treated, to obtain desired working time and physical properties, and treated for surface oxide reduction, in accordance with commercial practices. The particles are generally heat treated at a temperature in excess of 150° C. for a predetermined time in a protective atmosphere.

Although the present invention is believed to be adaptable to all amalgamable dental alloys, it is believed to be particularly beneficial for those that contain at least 30% silver and 15% tin. Typical amalgamable dental alloys are disclosed in U.S. Pat. Nos. 3,871,876 and 4,374,085. The alloys of these patents usually contain at least 40% silver, at least 20% tin and at least 10% copper.

The amalgamable dental alloy produced in accordance with the present invention may be used as is or blended with additives to achieve desired handling characteristics and physical properties. For example, from 3 to 10% silver has been added to the worked particles to enhance their mold adaptation characteristics.

The following examples are illustrative of several aspects of the invention.

Particles of Alloys A, B and C were produced in accordance with the present invention. They were water atomized at a pressure of approximately 1500 pounds per square inch so as to form irregularly shaped particles having a particle size in excess of 150 microns, mechanically worked in a high speed multiple hammer mill so as to fracture and change their shape, classified finer than 53 microns, and heat treated at a temperature of approximately 200° C. for 2 hours in an argon atmosphere. The nominal chemistry of the particles appears hereinbelow in Table I.

TABLE I

| ALLOY | COMPOSITION (wt. %) | | | | |
|---|---|---|---|---|---|
| | Ag | Cu | Sn | Pd | Zn |
| A | 49.5 | 20.0 | 30.0 | 0.5 | — |
| B | 58.75 | 13.0 | 28.0 | — | 0.25 |
| C | 43.4 | 25.2 | 31.4 | — | — |

Several leakage tests were performed with Alloys A, B and C. Alloys A and B were tested without additions thereto. Alloy B was also tested with an addition of 6% silver. Alloy C was mixed with a spherical alloy (35% silver, 32% copper, 32.5% tin and 0.5% palladium) having a particle size less than 44 microns, in the ratio of 2 parts Alloy C and 1 part spherical alloy and tested with additions of 4 and 8% silver. The test procedure is described in an article entitled, "Marginal Leakage of Dental Amalgam." The article appears in the Aug. 11, 1983 issue of *Operative Dentistry*. It was written by F. Fanian, F. Hadavi and K. Asgar. Briefly stated, the test involves condensing amalgam into a fixed size and shape cavity, forcing argon gas through it and collecting the amount of gas that passes through. The results of the test appear hereinbelow in Table II.

TABLE II

| ALLOY | LEAKAGE IN 10 MINUTES (milliliters) |
|---|---|
| A | 5 |
| B | 7 |
| B + 6% Ag | 4 |
| C + spherical alloy + 4% Ag | Less than 1 |
| C + spherical alloy + 8% Ag | Less than 1 |

Leakage tests were also performed on five commercial ad-mixed type alloys (Alloys D, E, F, G and H) and an irregularly shaped atomized alloy (Alloy I). The results of the tests appear hereinbelow in Table III.

TABLE III

| ALLOY | LEAKAGE IN 10 MINUTES (milliliters) |
|---|---|
| D | 13 |
| E | 10 |
| F | 12 |
| G | 5 |
| H | 1 |
| I | 11 |

A comparison of Tables II and III reveals that the leakage rate for the alloys prepared in accordance with the present invention is less than that for the tested commercially available irregularly shaped atomized alloy and comparable to or lower than that for the ad-mixed alloys. Table II also shows the benefit of adding pure silver to the alloy.

The important point to keep in mind in evaluating the data of Tables II and III is not the values by themselves but how they compare to others obtained under similar test conditions. Testing of seven commercially available spherically shaped atomized alloys, under similar conditions, produced values from 16 to 70.

The physical properties of amalgams formed from Alloys A, B, B with 6% silver, C with spherical alloy and 4% silver and C with spherical alloy and 8% silver were compared with the physical properties of three ad-mixed type alloys. The nominal chemistry of the three ad-mixed type alloys (Alloys J, K and L) appears hereinbelow in Table IV.

TABLE IV

| ALLOY | COMPOSITION (wt. %) | | | | |
|---|---|---|---|---|---|
| | Ag | Cu | Sn | Pd | Zn |
| J | 65.0 | 13.0 | 21.3 | — | 0.7 |
| K | 52.5 | 17.5 | 29.7 | 0.3 | — |
| L | 58.7 | 19.3 | 21.3 | — | 0.7 |

The test results appear hereinbelow in Table V.

TABLE V

| | PROPERTIES | | | | | | | |
|---|---|---|---|---|---|---|---|---|
| | Compressive Strength (pounds per square inch) | | Tensile Strength (pounds per square inch) | | Creep | Dimensional Change (Microns/ | Corrision** | |
| ALLOY | 1 Hour | 24 Hours | 15 Minutes | 24 Hours | % | centimeter) | Mahler | Marek |
| A | 22,750 | 62,600 | 970 | 6,750 | 0.01 | −4.4 | 22 | 4.6 |
| B | 26,000 | 62,400 | 1140 | 7,800 | 0.05 | −4.3 | 27 | 29 |
| B + 6% Ag | 22,000 | 59,800 | 860 | 7,650 | 0.04 | +3.6 | 28 | 21 |
| C + 4% Ag* | 24,300 | 73,000 | 1450 | 8,400 | 0.02 | −2.9 | 13 | 43 |
| C + 8% Ag* | 24,600 | 66,450 | 1280 | 8,000 | 0.03 | +5.5 | 14 | 29 |
| J | 22,500 | 60,500 | 900 | 8,200 | 0.5 | −4.0 | 8 | 10 |
| K | 30,800 | 66,400 | 1470 | 8,400 | 0.2 | −7.5 | 7.5 | 7 |
| L | 12,500 | 55,700 | 560 | 8,200 | 0.7 | −6.7 | 10 | 13 |

*With spherical alloy
**The corrosion values for Alloys A, B and C would have been lower had these alloys been treated to reduce surface oxides.

Table V clearly shows that alloys prepared in accordance with the present invention have physical properties comparable to ad-mixed type alloys. The Mahler and Marek corrosion tests are respectively described in the following publications: "Creep and Corrosion of Amalgam," by D. B. Mahler, J. E. Adey and M. Marek, *Journal of Dental Research,* 61:33, January, 1982; and "Corrosion Test for Dental Amalgam," by M. Marek, *Journal of Dental Research,* 59:63, January, 1980.

It will be apparent to those skilled in the art that the novel principles of the invention disclosed herein in connection with specific examples thereof will suggest various other modifications and applications of the same. It is accordingly desired that in construing the breadth of the appended claims they shall not be limited to the specific examples of the invention described herein.

We claim:

1. In a process for producing an amalgamable alloy, which process includes the steps of: producing a melt of an amalgamable alloy; atomizing said alloy so as to form particles thereof; collecting said particles; drying said particles; classifying said particles; and heat treating said particles; the improvement comprising the steps of: atomizing said alloy so as to form particles which are primarily irregular in shape and generally larger than 150 microns in their longest dimensions; mechanically working said particles so as to fracture and change the shape thereof, substantially all of said mechanically worked particles being of a size less than 53 microns in their longest dimension; and treating said particles so as to reduce oxides from the surface thereof.

2. The process according to claim 1, wherein said alloy is water atomized at a pressure of from 700 to 2,300 pounds per square inch.

3. The process according to claim 2, wherein said alloy is water atomized at a pressure of from 1,000 to 2,000 pounds per square inch.

4. The process according to claim 1, wherein said amalgamable alloy contains at least 30% silver and at least 15% tin.

5. The process according to claim 1, wherein said amalgamable alloy contains at least 40% silver, at least 20% tin and at least 10% copper.

6. The process according to claim 1, including the step of blending from 3 to 10% silver with the worked particles.

* * * * *